US007764762B2

(12) United States Patent
Sendai

(10) Patent No.: US 7,764,762 B2
(45) Date of Patent: Jul. 27, 2010

(54) RADIATION CT APPARATUS AND RADIATION CT METHOD

(75) Inventor: Tomonari Sendai, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 12/405,848

(22) Filed: Mar. 17, 2009

(65) Prior Publication Data

US 2009/0232271 A1 Sep. 17, 2009

(30) Foreign Application Priority Data

Mar. 17, 2008 (JP) ............................. 2008-066990
Nov. 5, 2008 (JP) ............................. 2008-283904

(51) Int. Cl.
*A61B 6/00* (2006.01)
*H05G 1/60* (2006.01)
*H05G 1/64* (2006.01)
*A61B 6/04* (2006.01)

(52) U.S. Cl. ............................. 378/8; 378/19; 378/98.3; 378/37

(58) Field of Classification Search ............ 378/4, 378/8, 19, 37, 98.3
See application file for complete search history.

(56) References Cited

U.S. PATENT DOCUMENTS

| 5,539,797 A * | 7/1996 | Heidsieck et al. ............. 378/37 |
| 6,418,186 B1 * | 7/2002 | Kawai et al. .................. 378/19 |
| 6,842,502 B2 * | 1/2005 | Jaffray et al. ................. 378/65 |
| 7,016,465 B2 * | 3/2006 | Kamegawa .................. 378/63 |
| 7,555,096 B2 * | 6/2009 | Urushiya ..................... 378/19 |
| 2006/0018426 A1 * | 1/2006 | Bruder et al. ................. 378/19 |

FOREIGN PATENT DOCUMENTS

JP        2006-158423 A        6/2006

* cited by examiner

*Primary Examiner*—Irakli Kiknadze
(74) *Attorney, Agent, or Firm*—Sughrue Mion, PLLC

(57) ABSTRACT

A region of interest information obtaining section obtains the size and position of a region of interest within a radiation image of a subject. A position calculating section calculates positions for a radiation source and a detecting panel that enable appropriate radiation imaging of the region of interest, employing the region of interest information. A moving section moves the radiation source and the detecting panel to the positions calculated by the position calculating section. Radiation images of the subject are obtained while rotating the radiation source and the detecting panel about a rotating axis that passes through a predetermined position at which the subject is placed.

27 Claims, 7 Drawing Sheets

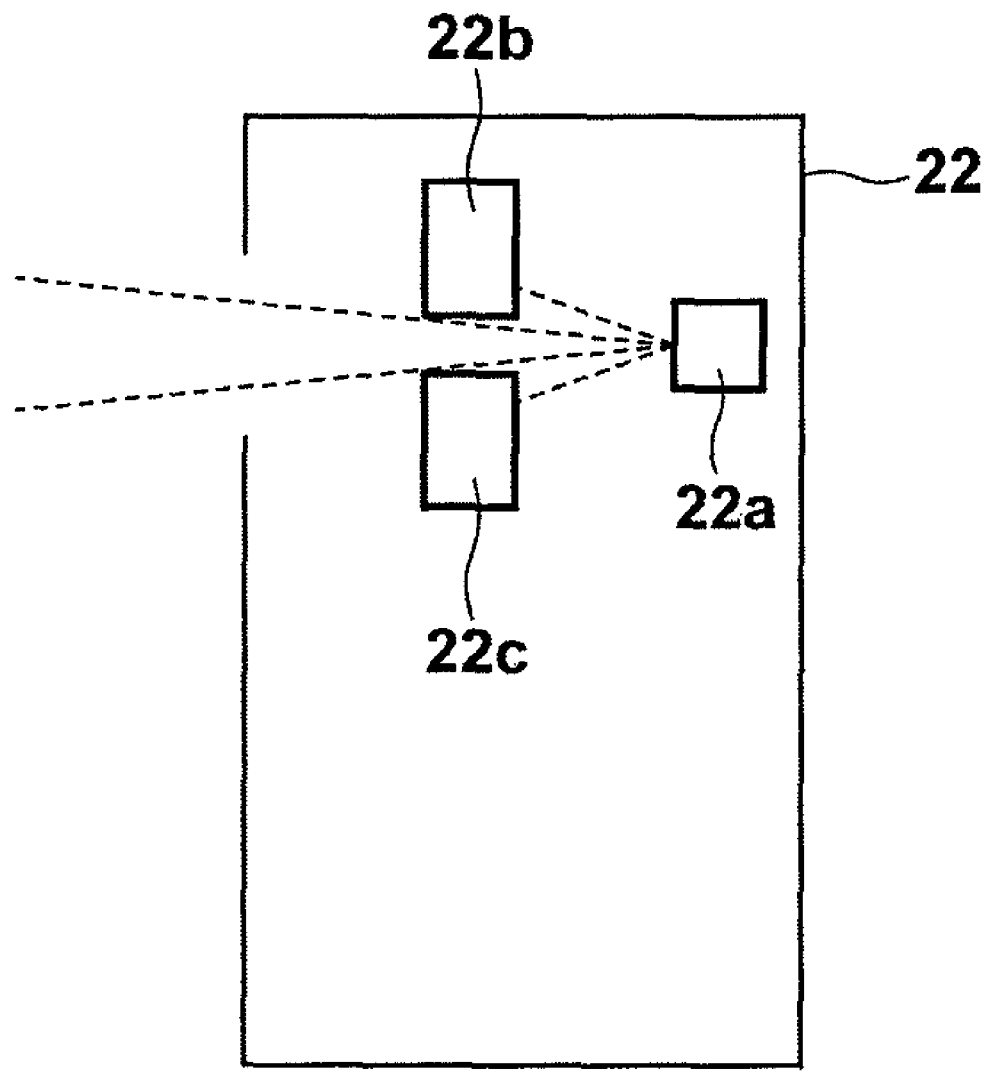

RADIATION CT APPARATUS AND RADIATION CT METHOD

BACKGROUND OF THE INVENTION

1. Field of the Invention

The present invention is related to a radiation CT apparatus and an imaging method to be employed by a radiation CT apparatus. More specifically, the present invention is related to a radiation CT apparatus that obtains radiation images of subjects by sequential imaging, and an imaging method to be employed by such a radiation CT apparatus.

2. Description of the Related Art

There are known radiation CT apparatuses for performing radiation imaging of breasts. A bed type apparatus is known as this type of radiation CT (Computed Tomography) apparatus (refer to U.S. Patent Application Publication No. 20040081273).

In this radiation CT apparatus, a patient lays face down on a support base, and the patient's breast is fitted through an opening which is formed in the support base. When performing radiation imaging, a radiation source and a detecting panel are provided such that they face each other with the breast positioned below a bed interposed therebetween. Then, radiation imaging of the breast is sequentially performed while integrally rotating the radiation source and the detecting panel about an axis of rotation that passes vertically through the breast, to generate a radiation CT image. During the radiation imaging operation, the relative positions between the radiation source and the detecting panel are changed in the direction that they face each other in, to enable changes in the magnification rate of the breast.

Japanese Unexamined Patent Publication No. 2006-158423 discloses an image diagnosis apparatus that obtains images of subjects employing lower dosage radiation than the dosage of radiation employed for normal imaging, and employs the three dimensional data of the images obtained employing the lower dosage to design imaging plans.

There are cases in which small regions of the breast in which calcification has occurred appear in radiation images of breasts. In these cases, there is a desire for radiation images of the calcified small regions to be observed in greater detail. In addition, there are cases in which radiation images missing a portion of a breast are obtained, when radiation imaging of an extremely large breast is performed. There is a desire to perform radiation imaging such that radiation images that include the entire breast can be obtained, even if the breast is large.

Here, the imaging position must be set accurately with respect to a region of which a detailed image is desired. Otherwise, a radiation image in which a portion of the portion to be observed is missing may be obtained, or a radiation image having an insufficient magnification rate may be obtained. Therefore, there is a desire for radiation imaging to be performed with accurate setting of the imaging position.

Note that this problem is not limited to cases in which breasts are imaged, but is common to all types of radiation imaging by radiation CT apparatuses.

SUMMARY OF THE INVENTION

The present invention has been developed in view of the foregoing circumstances. It is an object of the present invention to provide a radiation CT apparatus and an imaging method to be employed by the radiation CT apparatus, which are capable of accurately setting imaging positions and adjusting imaging magnification rates during radiation imaging.

A first radiation CT apparatus of the present invention comprises:

a radiation source that emits radiation in a conical manner; and a detecting panel for detecting the radiation;

the radiation source and the detecting panel being provided facing each other with an axis of rotation that passes though a predetermined position therebetween;

radiation images of a subject placed at the predetermined position being imaged while rotating the radiation source and the detecting panel about the axis of rotation; and the position of at least one of the radiation source and the detecting panel being movable in the direction that they face each other in; and is characterized by further comprising:

region of interest information obtaining means, for obtaining region of interest information that represents the size and position of a region of interest within the radiation images, employing the radiation images of the subject;

position calculating means, for calculating positions for the radiation source and the detecting panel that enable appropriate radiation imaging of the region of interest, employing the region of interest information; and moving means, for moving the radiation source and the detecting panel to the positions calculated by the position calculating means.

A second radiation CT apparatus of the present invention comprises:

a radiation source that emits radiation in a conical manner; and a detecting panel for detecting the radiation;

the radiation source and the detecting panel being provided facing each other with an axis of rotation that passes though a predetermined position therebetween;

radiation images of a subject placed at the predetermined position being imaged while rotating the radiation source and the detecting panel about the axis of rotation; and the position of at least one of the radiation source and the detecting panel being movable in the direction that they face each other in; and is characterized by further comprising:

region of interest detecting means, for detecting the position of a region of interest within the radiation images, employing the radiation images that represent the subject; and means for moving the axis of rotation to the detected region of interest.

A first radiation CT imaging method of the present invention is an imaging method to be employed by a radiation CT apparatus comprising: a radiation source that emits radiation in a conical manner; and a detecting panel for detecting the radiation; the radiation source and the detecting panel being provided facing each other with an axis of rotation that passes though a predetermined position therebetween; and the position of at least one of the radiation source and the detecting panel being movable in the direction that they face each other in; characterized by comprising the steps of:

imaging radiation images of a subject placed at the predetermined position while rotating the radiation source and the detecting panel about the axis of rotation;

obtaining region of interest information that represents the size and position of a region of interest within the radiation images, employing the radiation images of the subject;

calculating positions for the radiation source and the detecting panel that enable appropriate radiation imaging of the region of interest, employing the region of interest information; and moving the radiation source and the detecting panel to the positions calculated by the position calculating means.

A second radiation CT imaging method of the present invention is an imaging method to be employed by a radiation CT apparatus comprising: a radiation source that emits radiation in a conical manner; and a detecting panel for detecting the radiation; the radiation source and the detecting panel being provided facing each other with an axis of rotation that passes though a predetermined position therebetween; and the position of at least one of the radiation source and the detecting panel being movable in the direction that they face each other in; characterized by comprising the steps of:

imaging radiation images of a subject placed at the predetermined position while rotating the radiation source and the detecting panel about the axis of rotation;

detecting the position of a region of interest within the radiation images, employing the radiation images that represent the subject; and moving the axis of rotation to the detected region of interest.

It is desirable for the second radiation CT apparatus of the present invention to further comprise:

position calculating means, for calculating positions for the radiation source and the detecting panel that enable appropriate radiation imaging of the region of interest, employing the size and the position of the region of interest; and moving means, for moving the radiation source and the detecting panel to the positions calculated by the position calculating means.

It is desirable for the region of interest information obtaining means of the first radiation CT apparatus of the present invention to obtain the information regarding the region of interest using images obtained by imaging in at least two directions.

It is desirable for the region of interest detecting means of the second radiation CT apparatus of the present invention to detect the information regarding the region of interest using images obtained by imaging in at least two directions.

The first and second radiation CT apparatuses of the present invention may further comprise:

a visible light imaging means for performing visible light imaging that converts the propagating region of radiation, which is emitted from the radiation source and detected by the detecting panel, to the visible range; and a visible light image display means for displaying visible light images obtained by the visible light imaging.

It is desirable for the region of interest information obtaining means of the first radiation CT apparatus of the present invention to obtain the information regarding the region of interest using one of the radiation images and the visible images obtained by imaging in at least two directions.

It is desirable for the region of interest detecting means of the second radiation CT apparatus of the present invention to detect the information regarding the region of interest using one of the radiation images and the visible images obtained by imaging in at least two directions.

The first and second radiation CT apparatuses of the present invention may further comprise:

means for controlling the aperture of a collimator of the radiation source such that the irradiation field of radiation irradiation is concentrated, based on the size and the position of the region of interest.

The first and second radiation CT apparatuses of the present invention may be configured such that the radiation source and the detecting panel are configured to be movable in the direction of the axis of rotation.

It is desirable for the radiation source and the detecting panel of the first and second radiation CT apparatuses of the present invention to be configured such that they are movable in the direction of the axis of rotation.

It is desirable for the first and second radiation CT apparatuses of the present invention to further comprise:

imaging magnification rate obtaining means, for obtaining an imaging magnification rate from the ratio of the distance from the axis of rotation to the radiation source and the distance from the axis of rotation to the detecting panel; and imaging magnification rate display means, for displaying the imaging magnification rate.

It is desirable for the first and second radiation CT apparatuses of the present invention to further comprise:

imaging magnification rate obtaining means, for obtaining an imaging magnification rate from the ratio of the distance from the axis of rotation to the radiation source and the distance from the axis of rotation to the detecting panel; and imaging magnification rate display means, for displaying the imaging magnification rate.

It is desirable for the first and second radiation CT apparatuses of the present invention to further comprise:

a radiation source distance measuring means, for measuring the distance from the subject placed at the predetermined position to the radiation source; and radiation source movement prohibiting means, for prohibiting movement of the radiation source toward the axis of rotation when the distance measured by the radiation source distance measuring means becomes less than or equal to a predetermined value.

It is desirable for the first and second radiation CT apparatuses of the present invention to further comprise:

a detecting panel distance measuring means, for measuring the distance from the subject placed at the predetermined position to the detecting panel; and detecting panel movement prohibiting means, for prohibiting movement of the detecting panel toward the axis of rotation when the distance measured by the detecting panel distance measuring means becomes less than or equal to a predetermined value.

It is desirable for the first and second radiation CT apparatuses of the present invention to further comprise:

radiation source contact detecting means, for detecting contact between the radiation source and the subject placed at the predetermined position; and at least one of:

radiation source movement prohibiting means, for prohibiting movement of the radiation source toward the subject based on the detection of contact; and radiation source contact notification means, for issuing notification regarding the detection of contact between the radiation source and the subject.

It is desirable for the first and second radiation CT apparatuses of the present invention to further comprise:

detecting panel contact detecting means, for detecting contact between the detecting panel and the subject placed at the predetermined position; and at least one of:

detecting panel movement prohibiting means, for prohibiting movement of the detecting panel toward the subject based on the detection of contact; and detecting panel contact notification means, for issuing notification regarding the detection of contact between the detecting panel and the subject.

It is desirable for the first and second radiation CT apparatuses of the present invention to further comprise:

means for storing image data that represents portions of the subject other than the region of interest at a predetermined resolution, and for storing image data that represents the region of interest within the subject at a resolution higher than the predetermined resolution.

The subject of imaging by the first and second radiation CT apparatuses of the present invention may be a breast.

Here, the "predetermined position" is a position at which the subject of radiation imaging is placed.

The phrase "appropriate radiation imaging of the region of interest" refers to radiation imaging that enables obtainment of a radiation image that includes the entire region of interest, and in which the region of interest is displayed at the largest possible size. Note that when attempting to perform appropriate radiation imaging of the region of interest, it is desirable to determine the positional relationship between imaging components and the region of interest such that the axis of rotation passes through the region of interest.

The phrase "the position of at least one of the radiation source and the detecting panel being movable in the direction that they face each other in" and the phrase "the radiation source and the detecting panel are configured to be movable in the direction of the axis of rotation" refer to cases in which: only the position of the detecting panel is movable with respect to the axis of rotation; only the position of the radiation source is movable with respect to the axis of rotation; moving the positions of the radiation source and the detecting panel with respect to the axis of rotation while maintaining a constant interval in the direction that they face each other in; and moving the positions of the radiation source and the detecting panel with respect to the axis of rotation, without maintaining a constant interval in the direction that they face each other in.

The phrase "storing image data that represents portions of the subject other than the region of interest at a predetermined resolution, and . . . storing image data that represents the region of interest within the subject at a resolution higher than the predetermined resolution" also refers to cases in which only image data that represent a specific portion of the region of interest are displayed with high resolution, and the other portions are displayed at a normal resolution.

In the first radiation CT apparatus of the present invention, the position of at least one of the radiation source and the detecting panel is movable in the direction that they face each other in. In addition, the first radiation CT apparatus of the present invention comprises the region of interest information obtaining means, for obtaining region of interest information that represents the size and position of a region of interest within the radiation images, employing the radiation images of the subject; the position calculating means, for calculating positions for the radiation source and the detecting panel that enable appropriate radiation imaging of the region of interest, employing the region of interest information; and the moving means, for moving the radiation source and the detecting panel to the positions calculated by the position calculating means. Therefore, radiation imaging, in which the imaging magnification rate can be adjusted by setting imaging positions such that a radiation image that includes the entire region of interest, and in which the region of interest is displayed at the largest possible size, can be obtained, becomes possible.

In the second radiation CT apparatus of the present invention, the position of at least one of the radiation source and the detecting panel is movable in the direction that they face each other in. In addition, the second radiation CT apparatus of the present invention comprises the region of interest detecting means, for detecting the position of a region of interest within the radiation images, employing the radiation images that represent the subject; and the means for moving the axis of rotation to the detected region of interest. Therefore, radiation imaging, in which the imaging magnification rate can be adjusted by accurately setting the imaging position of a radiation image of the region of interest, becomes possible.

A configuration may be adopted, wherein the region of interest information obtaining means of the first radiation CT apparatus of the present invention obtains the information regarding the region of interest using images obtained by imaging in at least two directions. In this case, imaging positions can be determined that enable obtainment of more accurate radiation images.

A configuration may be adopted, wherein the region of interest detecting means of the second radiation CT apparatus of the present invention detects the information regarding the region of interest using images obtained by imaging in at least two directions. In this case, imaging positions can be determined that enable obtainment of more accurate radiation images.

A configuration may be adopted, wherein the first and second radiation CT apparatuses of the present invention further comprise: a visible light imaging means for performing visible light imaging that converts the propagating region of radiation, which is emitted from the radiation source and detected by the detecting panel, to the visible range; and a visible light image display means for displaying visible light images obtained by the visible light imaging. In this case, imaging positions can be determined that enable obtainment of more accurate radiation images.

A configuration may be adopted, wherein the region of interest information obtaining means of the first radiation CT apparatus of the present invention obtains the information regarding the region of interest using one of the radiation images and the visible images obtained by imaging in at least two directions. In this case, imaging positions can be determined that enable obtainment of more accurate radiation images.

A configuration may be adopted, wherein the region of interest detecting means of the second radiation CT apparatus of the present invention detects the information regarding the region of interest using one of the radiation images and the visible images obtained by imaging in at least two directions. In this case, imaging positions can be determined that enable obtainment of more accurate radiation images.

The first and second radiation CT apparatuses of the present invention may further comprise means for controlling the aperture of a collimator of the radiation source such that the irradiation field of radiation irradiation is concentrated, based on the size and the position of the region of interest. In this case, the dosage of radiation irradiated on subjects can be minimized.

The first and second radiation CT apparatuses of the present invention may further comprise: imaging magnification rate obtaining means, for obtaining an imaging magnification rate from the ratio of the distance from the axis of rotation to the radiation source and the distance from the axis of rotation to the detecting panel; and imaging magnification rate display means, for displaying the imaging magnification rate. In this case, the imaging magnification rate can be easily recognized by an operator, and adjustments to the imaging magnification rate can be facilitated.

The first and second radiation CT apparatuses of the present invention may further comprise: means for storing image data that represents portions of the subject other than the region of interest at a predetermined resolution, and for storing image data that represents the region of interest within the subject at a resolution higher than the predetermined resolution. In this case, the image data can be stored more efficiently.

BRIEF DESCRIPTION OF THE DRAWINGS

FIG. 7 is a diagram that schematically illustrates the structure of a radiation source the radiation CT apparatus of the present invention.

BEST MODE FOR CARRYING OUT THE INVENTION

Figure 1:
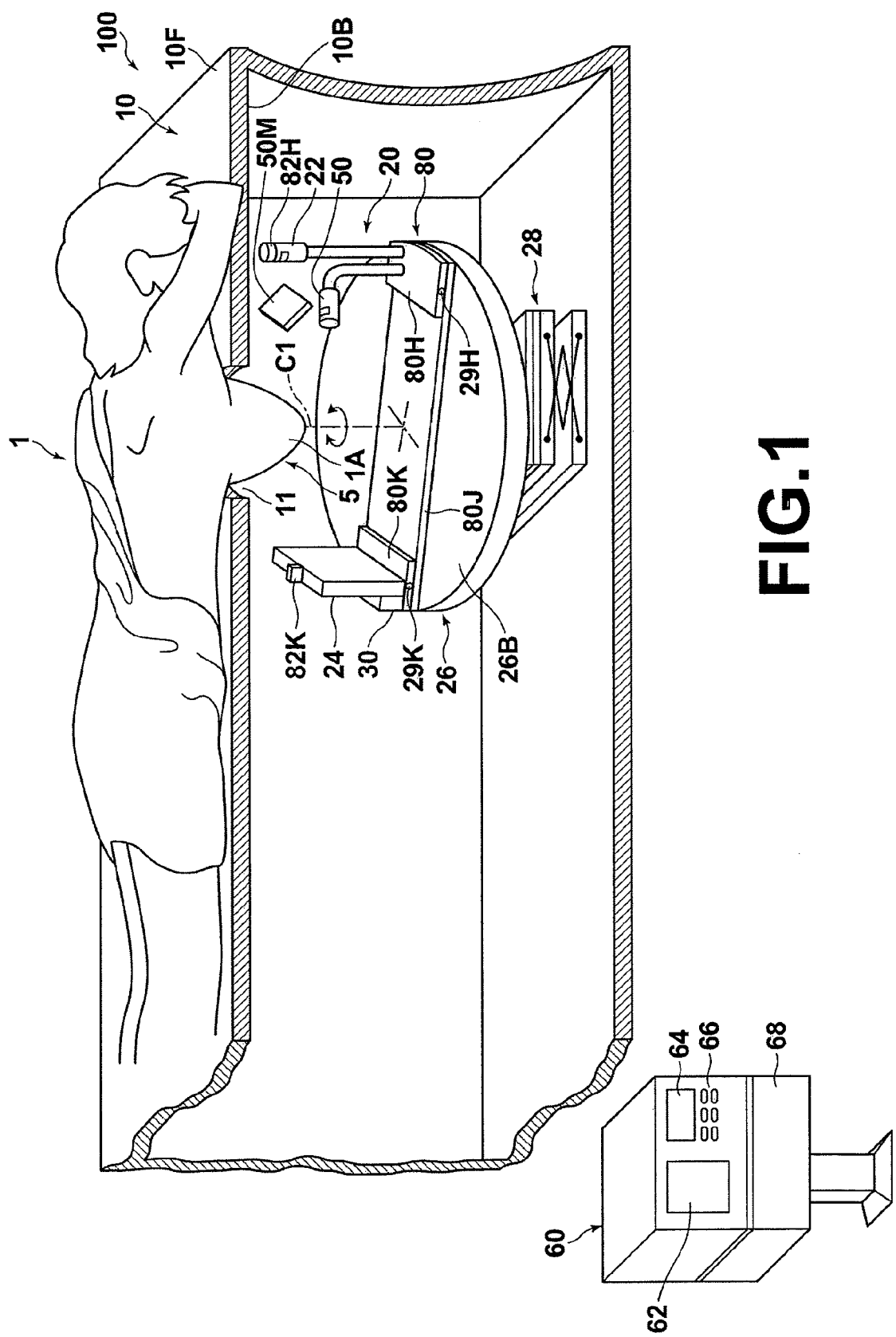
FIG. 1 is a perspective view that illustrates the schematic construction of a radiation CT apparatus according to an embodiment of the present invention.
Figure 2:
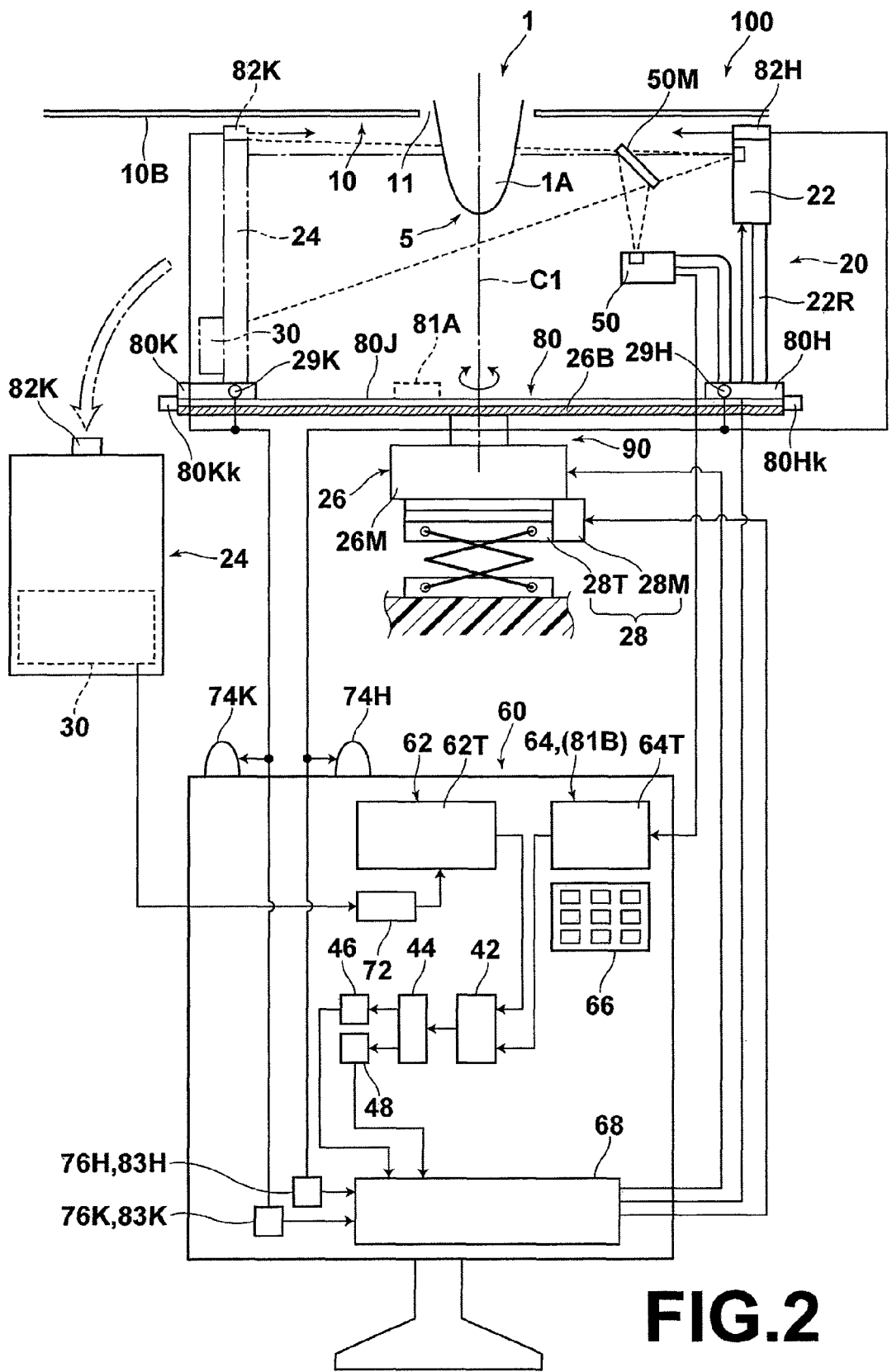
FIG. 2 is a block diagram for explaining the operation of the radiation CT apparatus of FIG. 1.

Hereinafter, embodiments of the present invention will be described with reference to the attached drawings. FIG. 1 is a perspective view that illustrates the schematic construction of an example of a radiation CT apparatus 100 according to an embodiment of the present invention. FIG. 2 is a block diagram for explaining the operation of the radiation CT apparatus 100 of FIG. 1.

The radiation CT apparatus 100 illustrated in FIG. 1 and FIG. 2 is equipped with: a bed portion 10 for supporting a patient 1, in which an opening 11 through which the breast 1A of the patient 1 is to pass through is formed; and an imaging section 20 that performs radiation imaging.

The imaging section 20 includes: a radiation source 22 that emits radiation in a conical manner (hereinafter, also referred to as "conical radiation"), a detecting panel 24 for detecting the radiation emitted by the radiation source 22; and a rotating section 26 for integrally rotating the radiation source 22 and the detecting panel 24 about an axis of rotation C1. The imaging section 20 is capable of being rotated 360° about the axis of rotation C1.

The radiation source 22 and the detecting panel 24 are provided facing each other with the axis of rotation C1 that passes through the breast 1A, which is placed at a predetermined position 5 through the opening 11, therebetween. Note that the predetermined position 5 is the position at which a subject is placed during radiation imaging. Here, the predetermined position 5 is the position at which the breast 1A, which is the subject of radiation imaging, is placed through the opening 11.

When radiation CT imaging is performed by the radiation CT apparatus 100, the positional relationships among the axis of rotation C1, the radiation source 22, and the detecting panel 24 are fixed.

A detecting surface, in which detection pixels that constitute the detecting panel 24 are arranged, may be a planar surface or a curved surface.

The imaging section 20 is provided at the underside 10B of the bed portion 10, opposite the upper side 10F that supports the patient 1.

In the radiation CT apparatus 100, conical radiation is emitted from the radiation source 22, passes through the breast 1A, and irradiated onto the detecting panel 22 while the radiation source 2 and the detecting panel 24 are integrally rotated about the axis of rotation that passes through the opening 11, formed in the bed portion 10 for supporting the patient. The radiation image which is recorded in the detecting panel 22 is read out. The above steps are repeated a plurality of times, and radiation images that represent the breast 1A are sequentially obtained. That is, a readout section 30 reads out the image signals recorded in the detection pixels of the detecting panel 24 for each imaging operation of the sequential imaging operations.

Further, the radiation CT apparatus 100 is equipped with an XYZ table 28. The XYZ table 28 enables movement of the radiation source 22 in the direction of the axis of rotation C1 as well as the directions perpendicular to the axis of rotation C1 (the X and Y directions). The entirety of the imaging section 20 is provided on the XYZ table 28. Therefore, the entirety of the imaging section 20 is movable in the direction of the axis of rotation C1 as well as the directions perpendicular to the axis of rotation C1 by movement of the XYZ table 28. The XYZ table 28 is constituted by a movable table portion 28T, which is constituted by known linear slide guides and the like, and a drive section 28M, which is constituted by a plurality of motors.

The lower surface of a rotating disk 26B of the rotating section 26 of the imaging section 20 is fixed on the XYZ table 28. The XYZ table 28 is capable of moving the imaging section 20 in the direction of the axis of rotation and the directions perpendicular to the axis of rotation, by being driven by the drive section 28M. It is also possible to move the imaging section 20 in the direction of the axis of rotation and the directions perpendicular to the axis of rotation, by manually moving the XYZ table 28.

Further, the radiation CT apparatus 100 is equipped with a visible light imaging section 50 for performing visible light imaging that converts the propagating region of radiation, which is emitted from the radiation source 22 and detected by the detecting panel 24, to the visible range. An optical image that represents the breast 1A, or an optical image that represents the detecting panel 24, is focused on and imaged by the visible light imaging section 50 via a mirror 50M. Here, the light receiving section of the visible light imaging section 50 has a conjugate optical relationship with the radiation emission point of the radiation source 22.

The mirror 50M transmits radiation. Therefore, it is not necessary to remove the mirror 50M from the propagating region of the radiation during radiation imaging. However, it is desirable to remove the mirror 50M from the propagating region of the radiation in the case that radiation images having high image quality are desired.

It is desirable for the visual field range of the visible light imaging section 50 to completely match the propagating region of radiation. However, portions of the propagating region of radiation, on which attention is not focused, may be outside the visual field range. Further, a portion of the propagating region may be outside the visual field range corresponding to insertion of structural components such as the mirror 50M.

Note that the visual light imaging section 50 is fixed onto a radiation source slide 80H to be described later. The positional relationship between the radiation source 22 and the visible light imaging section 50 is fixed. Accordingly, when radiation CT imaging is performed, the visible light imaging section 50, the radiation source 22, and the detecting panel 24 are integrally rotated about the axis of rotation C1 by a rotating motor 26M provided in the rotating section 26. That is, the imaging section 30 rotated about the axis of rotation C1 with respect to the XYZ table 28.

The radiation source 22 is configured to emit radiation at a normal dosage, and radiation at a lower dosage than the normal dosage. A radiation image display section 62 that displays radiation images obtained by radiation imaging using radiation at the normal dosage and by radiation imaging using radiation at the lower dosage is provided on a console 60.

Here, the propagating region of the lower dosage radiation and the propagating region of the normal dosage radiation emitted by the radiation source 22 match.

Note that the lower dosage radiation is used to position a subject or to determine radiation imaging conditions, for example. The lower dosage radiation is used to perform radiation imaging in which the influence of irradiation of radiation onto the subject is decreased as much as possible. Accordingly, radiation images obtained by radiation imaging employing the lower dosage radiation are not used for diagnosis, that is, these images are not employed for radiation CT imaging.

On the other hand, the normal dosage radiation is employed to obtain radiation images having image quality high enough to be utilized for diagnosis, and the normal dosage radiation is employed for radiation CT imaging.

A console 60, which is provided as a component of the radiation CT apparatus 100, includes: the radiation image display section 62 for displaying radiation images represented by the image signals read out from the detecting panel 24; a visible light image display section 64 for displaying visible light images obtained by visible light imaging by the visible light imaging section 50 in real time; an operating section 66 for performing various input operations; and the controller 68 for controlling the operations of the entire apparatus and the timing of each of the operations.

Note that pressure sensitive touch panels 62T and 64T, which are integrated with display screens, are provided in the radiation image display section 62 and the visible light image display section 64, respectively. Specific regions within displayed images can be directly specified by employing the touch panels, for example.

The console 60 equipped with the radiation image display section 62 and the visible light image display section 64 is provided in the vicinity of the imaging section 20. That is, the console 60 is provided near the imaging section 20 such that an operator who is performing radiation imaging can confirm the contents of display by the radiation image display section 62 and the visible light image display section 64 while moving the detecting panel 24, the radiation source 22, and the imaging section 20.

The radiation CT apparatus 100 is equipped with a slide table unit 80, which is provided on the rotating disk 26B and functions as a facing direction moving means. The slide table unit 80 enables movement of the radiation source 22 and the detecting panel 24 in the direction that they face each other in (hereinafter, also referred to as "the facing direction"), with respect to the axis of rotation C1.

The slide table unit 80 is equipped with: a slide base 80J, which is fixed on the rotating disk 26B; a radiation source slide 80H and a detecting panel slide 80K, which are provided on the slide base 80J and movable in the aforementioned facing direction; a radiation source slide driving section 80Hk for driving the radiation source slide 80H with a motor; and a detecting panel slide driving section 80Kk for driving the detecting panel slide 80K with a motor.

The detecting panel 24 is placed on the detecting panel slide 80K. The radiation source 22, the visible light imaging section 50, and the mirror 50M are placed on the radiation source slide 80H.

Note that it is possible to move the radiation source slide 80H and the detecting panel slide 80K manually along the slide base 80J, to move the radiation source 22 and the detecting panel 22 along the aforementioned facing direction with respect to the axis of rotation C1.

Note that the radiation CT apparatus 100 is also equipped with the following structural components. These components may be constituted by known mechanical elements, electrical elements, and the like.

A distortion sensor 29H that detects that the radiation source 22 has contacted the breast 1A is provided on the radiation source slide 80H. The distortion sensor 29H detects distortion which occurs in the radiation source slide 80H when the radiation source 22 contacts the breast 1A, thereby detecting contact between the radiation source 22 and the breast 1A. A detection signal is output from the distortion sensor 29H when contact between the radiation source 22 and the breast 1A is detected, and input to a contact notifying section 74F provided in the console 60. The contact notifying section 74H issues a notification that the radiation source 22 and the breast 1A are in contact.

Further, the detection signal output from the distortion sensor 29H is input to a radiation source movement preventing section 76H provided in the console 60. The radiation source movement preventing section 76H prevents further movement of the radiation source 22 in the direction toward the breast 1A. That is, the radiation source movement preventing section 76H prevents movement of the radiation source slide 80H toward the breast 1A by controlling the slide table unit 80 via the controller 68.

Similarly, a distortion sensor 29K that detects that the detecting panel 24 has contacted the breast 1A is provided on the detecting panel slide 80K. The distortion sensor 29K detects distortion which occurs in the detecting panel slide 80K when the detecting panel 24 contacts the breast 1A, thereby detecting contact between the detecting panel 24 and the breast 1A. A detection signal is output from the distortion sensor 29K when contact between the detecting panel 24 and the breast 1A is detected, and input to the contact notifying section 74F provided in the console 60. The contact notifying section 74H issues a notification that the detecting panel 24 and the breast 1A are in contact.

Further, the detection signal output from the distortion sensor 29K is input to a detecting panel movement preventing section 76K provided in the console 60. The detecting panel preventing section 76K prevents further movement of the detecting panel 24 in the direction toward the breast 1A. That is, the detecting panel movement preventing section 76K prevents movement of the detecting panel slide 80K toward the breast 1A by controlling the slide table unit 80 via the controller 68.

The radiation CT apparatus 100 is also equipped with: an imaging magnification rate obtaining section 81A, for obtaining an imaging magnification rate from the ratio of the distance from the axis of rotation C1 to the radiation source 22 and the distance from the axis of rotation C1 to the detecting panel 24; and an imaging magnification rate display section 81B, for displaying the imaging magnification rate. The magnification rate obtaining section 81A is built into the slide table unit 80.

The radiation CT apparatus 100 is further equipped with: a radiation source distance measuring section 82H, for measuring the distance from the breast 1A placed at the predetermined position to the radiation source 22; and a radiation source movement prohibiting section 83H, for prohibiting movement of the radiation source 22 toward the axis of rotation C1 when the distance measured by the radiation source distance measuring section 82H becomes less than or equal to a predetermined value. Here, the aforementioned radiation source movement preventing section 76H also functions as the radiation source movement preventing section 83H. The radiation source movement preventing section 83H prevents movement of the radiation source slide 80H toward the breast 1A by controlling the slide table unit 80 via the controller 68.

The radiation CT apparatus 100 is further equipped with: a detecting panel distance measuring section 82K, for measuring the distance from the breast 1A placed at the predetermined position to the detecting panel 24; and a detecting panel movement prohibiting section 83K, for prohibiting movement of the detecting panel 24 toward the axis of rotation C1 when the distance measured by the detecting panel distance measuring section 82K becomes less than or equal to a predetermined value. Here, the aforementioned detecting panel movement preventing section 76K also functions as the detecting panel movement preventing section 83K. The detecting panel movement preventing section 83K prevents movement of the detecting panel slide 80K toward the breast 1A by controlling the slide table unit 80 via the controller 68.

A region of interest obtaining section 42 also functions as a region of interest detecting section that detects the position of a region of interest.

A moving section 90 that moves the radiation source 22 and the detecting panel 24 to positions determined by a position calculating section 44 is constituted by at least: the controller 68; the rotating section 26; the slide table unit 80; the XYZ table 28; an imaging magnification control section 46; and an imaging position control section 48. In addition, the moving section 90 also functions to move the axis of rotation to a region of interest Kb which is detected by the region of interest detecting section.

Hereinafter, the operation of the radiation CT apparatus 100 will be described.

Figure 3A:
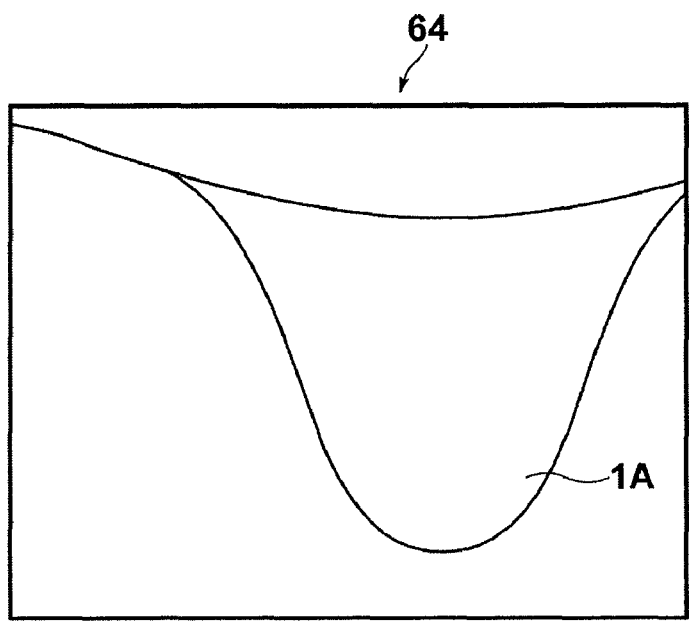
FIG. 3A is a diagram that illustrates a visible light image which is displayed prior to changing the imaging magnification rate.
Figure 3B:
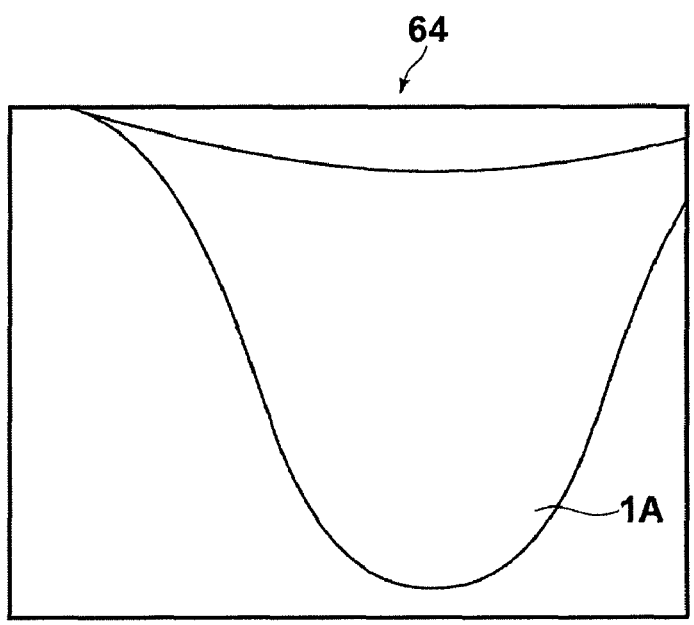
FIG. 3B is a diagram that illustrates a visible light image which is displayed after changing the imaging magnification rate.
Figure 4A:
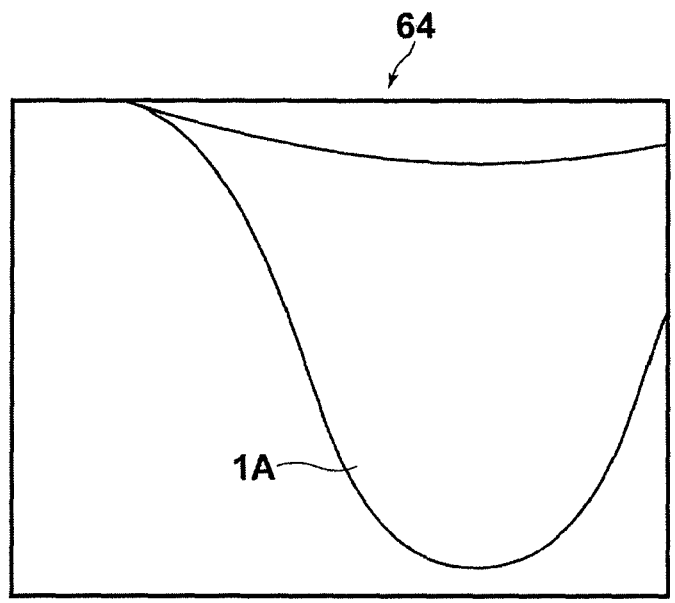
FIG. 4A is a diagram that illustrates a state in which a breast is not positioned at an axis of rotation.
Figure 4B:
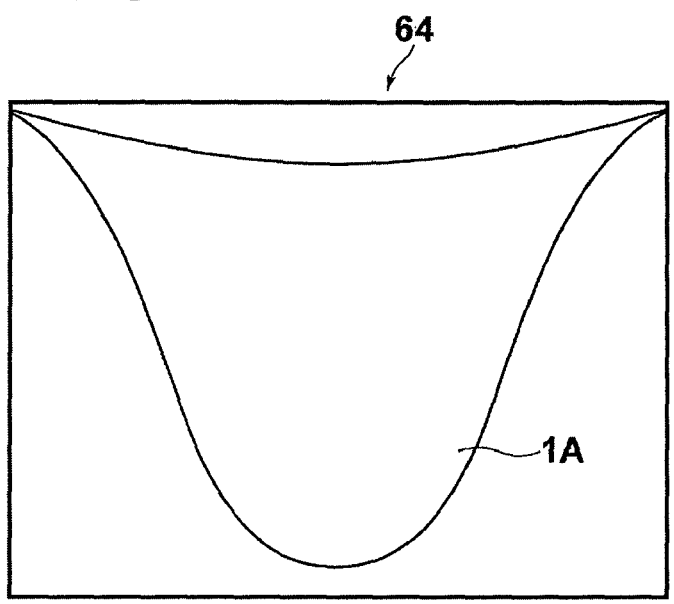
FIG. 4B is a diagram that illustrates a state in which adjustments have been performed such that the center of the breast is positioned at the axis of rotation.

FIG. 3A and FIG. 3B are diagrams that illustrate the manner in which visible light images are utilized to move the radiation source and the detecting panel along the direction that they face each other in, to change the imaging magnification rate for radiation imaging. FIG. 3A is a diagram that illustrates a visible light image which is displayed prior to changing the imaging magnification rate, and FIG. 3B is a diagram that illustrates a visible light image which is displayed after changing the imaging magnification rate. FIG. 4A and FIG. 4B are diagrams that illustrate the manner in which visible light images are utilized to move the imaging section to adjust the position of a breast with respect to the axis of rotation. FIG. 4A is a diagram that illustrates a state in which the breast is not positioned at the axis of rotation, and FIG. 4B is a diagram that illustrates a state in which adjustments have been performed such that the center of the breast is positioned at the axis of rotation.

A patient 1 lies face down on the bed portion 10, passes her breast 1A through the opening 11 of the bed portion 10, and places her breast 1A at the predetermined position.

The operating section 66 is manipulated by an operator to cause a visible light image to be displayed by the visible light image display section 64. Here, the imaging range of the visible light image that represents the breast 1A displayed by the visible light image display section 64 and the imaging range of a radiation image that represents the breast 1A obtained by radiation imaging match.

The operator moves the radiation source slide 80H and the detecting panel slide 80K while viewing the visible light image display section 64 (refer to FIG. 3A), to move the radiation source 22 and the detecting panel 24 in the aforementioned facing direction. Thereby, for example, the region of the visible light image in which the breast 1A is pictured is magnified as illustrated in FIG. 3B, for example. This range matches the imaging range of radiation imaging. The imaging magnification rate for radiation imaging of the breast 1A can be changed in this manner.

Note that the imaging magnification rate increases as the radiation source 22 is moved closer to the axis of rotation C1. The imaging magnification rate also increases as the detecting panel 24 is moved further from the axis of rotation C1.

Note that the radiation source 22 and the detecting panel 24 may be moved with respect to the axis of rotation, while maintaining a constant interval between the radiation source 22 and the detecting panel 24.

Further, the XYZ table 28 is manually operated to move the imaging section 20 in the direction of the axis of rotation as well as the directions perpendicular to the axis of rotation, to adjust the position of the breast 1A displayed by the visible light image display section 64 (refer to FIG. 4A). Thereby, the position of the breast 1A with respect to the axis of rotation C1 in radiation images can be changed. Accordingly, adjustments to the imaging position are enabled, and the central portion of the breast 1A can be positioned on the axis of rotation C1 (refer to FIG. 4B).

Note that in the case that adjustments are performed on both the imaging magnification rate and the imaging position, it is desirable for the imaging position to be adjusted first to set the central portion of the subject on the axis of rotation, then to adjust the imaging magnification rate. This is because if the imaging section 20 is moved in the direction in which the radiation source 22 and the detecting panel face each other by the XYZ table 28, the distance from the subject to the radiation source 22 and the distance from the subject to the detecting panel 24 changes. That is, the imaging magnification rate will be changed during adjustment of the imaging position.

Note that the XYZ table 28 that causes the imaging section 20 to be movable with respect to the bed portion 10 may only enable movement of the imaging section 20 in the direction of the axis of rotation and a direction perpendicular to the axis of rotation. By adopting this configuration, changes to the imaging magnification rate caused by the XYZ table 28 moving the imaging section 20 can be prevented.

Note that the mechanism by which the imaging section 20 is relatively moved with respect to the predetermined position at which the subject is placed in the direction of the axis of rotation and the directions parallel thereto is not limited to the XYZ table 28. Alternatively, a support base moving mechanism may be provided that moves the bed portion 10, in which the opening 11 is formed and is a support base for supporting the patient 1, in the direction of the axis of rotation and the directions perpendicular to the axis of rotation.

Further, neither the XYZ table 28 nor the aforementioned support base moving mechanism may be employed. That is, only the imaging magnification rate may be adjusted, without adjusting the imaging position.

Note that the adjustment of the imaging magnification rate may be performed automatically, by employing the region of interest obtaining section 42, the position calculating section 44, the slide table unit 80 that functions as a facing direction movement means, the XYZ table 28 that functions as an imaging position moving means, the imaging magnification rate control section 46, and the imaging position control section 48 in the following manner.

Figure 5A:
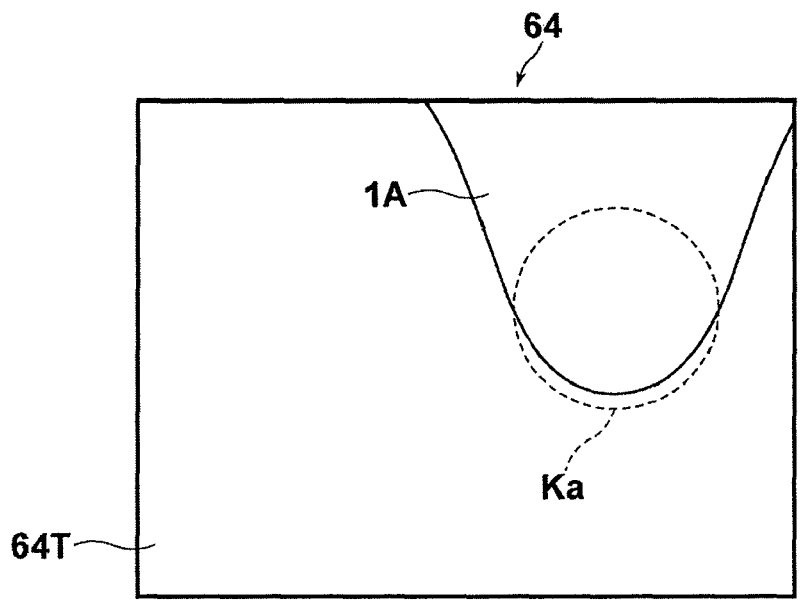
FIG. 5A is a diagram that illustrates a visible light image prior to automatic adjustment of the imaging magnification rate and the imaging position.
Figure 5B:
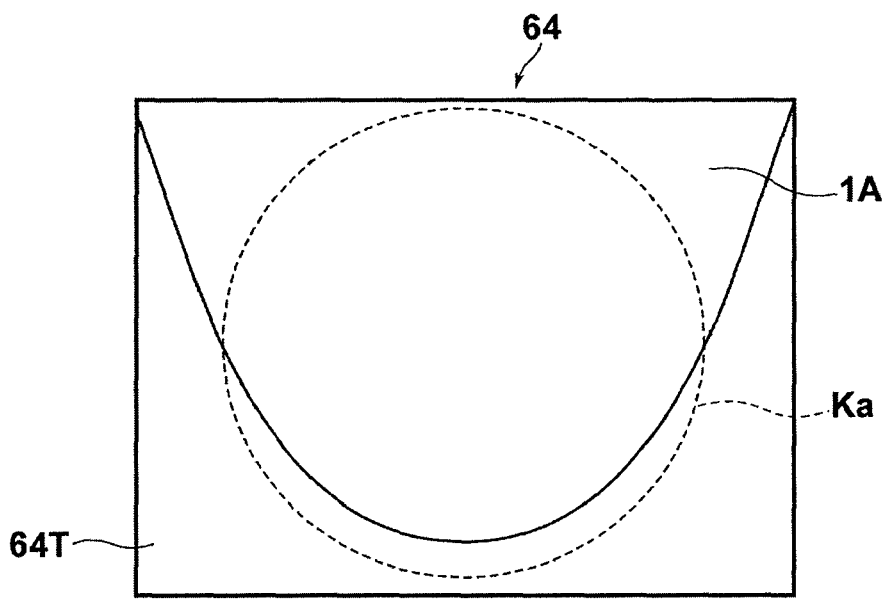
FIG. 5B is a diagram that illustrates a visible light image following automatic adjustment of the imaging magnification rate and the imaging position.

FIG. 5A and FIG. 5B are diagrams that illustrate the manner in which the imaging magnification rate and the imaging position are automatically adjusted such that a region of interest within a breast is imaged appropriately. FIG. 5A is a diagram that illustrates a visible light image prior to automatic adjustment of the imaging magnification rate and the imaging position. FIG. 5B is a diagram that illustrates a visible light image following automatic adjustment of the imaging magnification rate and the imaging position.

The console 60 of the radiation CT apparatus 100 is equipped with: the region of interest information obtaining section 42 for obtaining region of interest information that indicates the size and position of a region of interest Ka within a visible light image, employing the visible light image that represents a breast 1A, which is placed at the predetermined position, obtained by a visible light imaging operation; and the position calculating section 44 for calculating positions for the radiation source 22 and the detecting panel 24 along the aforementioned facing direction that enable appropriate radiation imaging of the region of interest Ka, and the position of the imaging section 20 with respect to the breast 1A, employing the region of interest information.

Further, the console 60 is equipped with: the slide table unit 80 for moving of the radiation source 22 and the detecting panel 24 in the direction that they face each other in, with respect to the axis of rotation C1; and the imaging magnification control section 46 for controlling the slide table unit 80 via the controller 68 such that the positions of the radiation source 22 and the detecting panel 24 with respect to the axis of rotation C1 match those which are calculated by the position calculating section 44.

Still further, the console 60 is equipped with: the XYZ table 28 for moving the imaging section 20 with respect to the breast 1A; and the imaging position control section 48, for controlling the XYZ table 28 via the controller 68 such that the position of the imaging section 20 matches that which is calculated by the position calculating section 44.

A visible light image of a breast 1A, obtained by visible light imaging performed by the visible light imaging section 50 according to operator input to the operating section 66 in the same manner as described above. Thereafter, the radiation source 22, the detecting panel 24, and the imaging section 20 are positioned automatically to adjust the imaging magnification rate and the imaging position, as will be described below.

First, an operator specifies a region of interest Ka within a visible light image, which is obtained by visible light imaging, using the touch panel 64T which is integrated with the visible light image display section 64, as illustrated in FIG. 5A.

Here, it is desirable for the region of interest Ka to be specified within a plurality of visible light images, which are obtained with the imaging section 20 at different rotational positions about the axis of rotation C1. In addition, it is also desirable for the region of interest to be specified within a plurality of visible light images and a plurality of radiation images which are obtained with the imaging section 20 at different rotational positions. By specifying the region of interest Ka in this manner, the position and size of the region of interest Ka can be specified more accurately.

Next, the region of interest information obtaining section 42 obtains region of interest information that indicates the size and position of the region of interest Ka within the breast 1A, which is specified in the visible light image being displayed by the visible light image display section 64. Here, the region of interest information obtaining section 42 also functions as a region of interest detecting means for detecting a region of interest Kb.

The position calculating section 44 calculates the position of the imaging section 20 with respect to the region of interest Ka, and the positions for the radiation source 22 and the detecting panel 24 with respect to the axis of rotation C1 that enable appropriate radiation imaging of the region of interest Ka, employing the obtained region of interest information.

That is, the position calculating section 44 calculates the position of the imaging section 20 with respect to the region of interest Ka at which the axis of rotation C1 passes through the region of interest and the region of interest is positioned at the center of the visible light image, and calculates the positions for the radiation source 22 and the detecting panel 24 with respect to the axis of rotation C1 such that the visible light image appropriately includes the region of interest when imaging is performed with the imaging section 20 at the above calculated position.

Note that in the case that a visible light image, which is displayed by the visible light image display section 64, appropriately includes the region of interest, a radiation image obtained by radiation imaging will also appropriately include the region of interest.

Thereafter, the results of calculations by the position calculating section 44 are input to the imaging magnification rate control section 46 and the imaging position control section 48.

The imaging position control section 48 to which the results of calculations are input controls the XYZ table 28 via the controller, to position the imaging section 20 with respect to the region of interest Ka. That is, the imaging section 20 is positioned such that the axis of rotation C1 passes through the region of interest Ka and the region of interest Ka is positioned at the center of the visible light image. After this positioning operation, the adjustment of the imaging position is complete. That is, the moving section 90 functions to move the axis of rotation C1 to the position of the region of interest Kb which is detected by the region of interest information obtaining section 42 functioning as the region of interest detecting section.

Meanwhile, the imaging magnification rate control section 46 to which the results of calculations are input controls the slide table unit 80 via the controller 68, and positions the radiation source 22 and the detecting panel 24 with respect to the axis of rotation C1. After this positioning operation, the adjustment of the imaging magnification rate is complete. In this manner, the moving section 90 functions to move the radiation source 22 and the detecting panel 24 to the positions calculated by the position calculating section 44.

As a result, the visible light image displayed by the visible light image display section 64 appropriately includes the region of interest Ka, as illustrated in FIG. 5B. Thereby, radiation CT imaging, which is capable of obtaining radiation images that appropriately represent the region of interest Ka, is enabled.

Alternatively, only the detecting panel 24 may be moved with respect to the axis of rotation C1.

A case in which both the imaging magnification rate and the imaging position are adjusted has been described above. However, the present invention is not limited to such a configuration, and only the imaging magnification rate may be adjusted. That is, the radiation source 22 and the detecting panel 24 may be moved by the slide table unit 80, without the XYZ table 28 moving the imaging section 20. In this case, the imaging magnification rate is adjusted such that the region of interest Ka will not be displayed at the center of the visible light image, but the entirety of the region of interest Ka is included in the visible light image, and the region of interest Ka is displayed as large as possible. Appropriate radiation imaging of the region of interest refers to radiation imaging that enables obtainment of a radiation image that includes the entire region of interest, and in which the region of interest is displayed at the largest possible size. Radiation imaging is performed under conditions such that the region of interest is imaged appropriately.

After the radiation source 22, the detecting panel 24, and the imaging section 20 are positioned in this manner, a first radiation imaging operation of the breast 1A is performed by the imaging section 20 according to an operation of the operating section 66. Thereby, a radiation image that represents the breast 1A is recorded in the detecting panel 24.

The readout section 30 reads out the image signals which are recorded in the detection pixels within the necessary readout region 24A, and outputs the image signals to an image processing section 72 of the console.

The image processing section 72 stores the image signals input thereto from the readout section 30.

When all of the image signals recorded in the detecting panel 24 are read out by the readout section 30, the detecting panel 24 is in a state in which a next radiation imaging operation is possible. At this point in time, a second radiation imaging operation is executed by the imaging section 20, and the processes described above are repeated. Thereby, image signals output from the readout section 30 are accumulated in the image processing section 72.

Thereafter, radiation imaging operations by the imaging section 20 and readout of image signals by the readout section 30 are repeatedly executed, and the sequential imaging of the breast 1A is completed.

Here, the movement of the imaging section 20 in the direction perpendicular to the axis of rotation C1 by the XYZ table 28 prior to the first radiation imaging operation has positioned the imaging section 20 such that the axis of rotation C1 passes through the region of interest Ka within the breast 1A. Therefore, variations in the position of the region of interest Ka with respect to the irradiation fields of radiation that change during the sequential imaging operations can be suppressed. That is, the region of interest Ka can be maintained at a position at the center of the irradiation fields.

When the sequential imaging operations are completed, the image signals that represent each of the radiation images, which have been read out from the detecting panel 24 for each radiation imaging operation, are accumulated in the image processing section 72. The image processing section 72 reconstitutes the image signals that represent each of the radiation images, to generate image signals that represent a radiation CT image. The image signals that represent the radiation CT image are input to the radiation image display section 62, and the radiation image display section 62 displays the radiation CT image.

As described above, the radiation CT apparatus 100 is capable of adjusting the imaging magnification rate during radiation imaging easily.

In the embodiment described above, the imaging magnification rate and the imaging position were adjusted employing the visible light images obtained by the visible light imaging section 50. However, the present invention is not limited to such a configuration. For example, radiation images, which are obtained by radiation imaging using low dosage radiation, may be employed to adjust the imaging magnification rate and the imaging position. If this configuration is adopted, the imaging magnification rate and the imaging position may be set such that radiation images, in which a diseased region Kb within the breast 1A which is not displayed by the visible light image display section 64, is magnified.

Hereinafter, a case will be described in which radiation images, which are obtained by radiation imaging using low dosage radiation, are employed to adjust the imaging magnification rate and the imaging position.

The operating section 66 is manipulated by an operator to cause low dosage radiation to be repeatedly irradiated toward the breast 1A with constant temporal intervals therebetween. Radiation images, which are recorded in the detecting panel 24 by the low dosage radiation imaging operations, are read out by the readout section 30, and sequentially displayed by the radiation image display section 62.

The operator operates the slide table unit 80 and the XYZ table 28, to manually adjust the imaging magnification rate and the imaging position. The imaging magnification rate and the imaging position for radiation imaging of the breast 1A can be adjusted in this manner.

Note that the adjustment of the imaging magnification rate and the imaging position using the radiation images obtained by low dosage radiation imaging may be performed automatically, by employing the region of interest obtaining section 42, the position calculating section 44, the slide table unit 80, the XYZ table 28, the imaging magnification rate control section 46, and the imaging position control section 48 in the following manner.

Figure 6A:
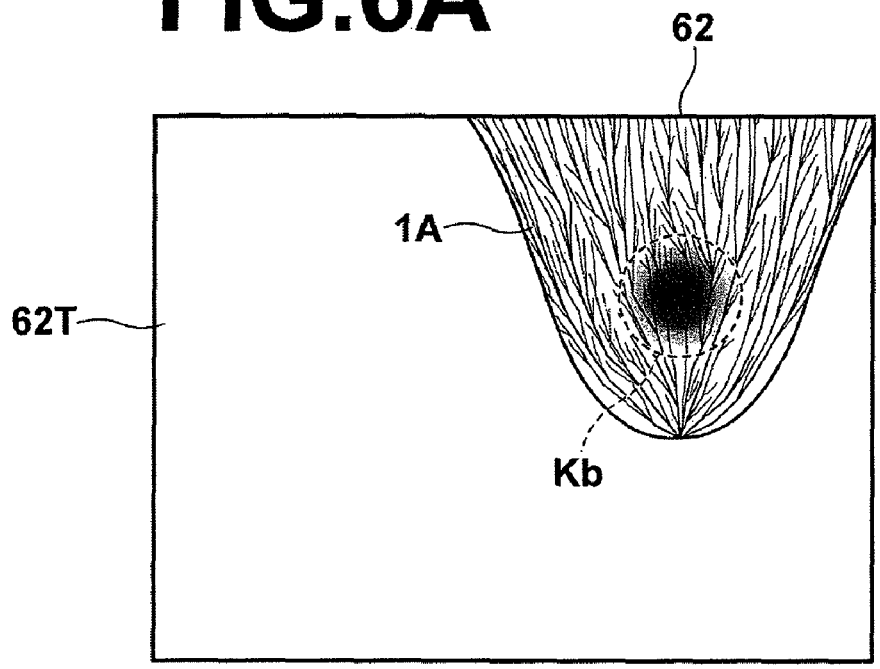
FIG. 6A is a diagram that illustrates a radiation image prior to automatic adjustment of the imaging magnification rate and the imaging position.
Figure 6B:
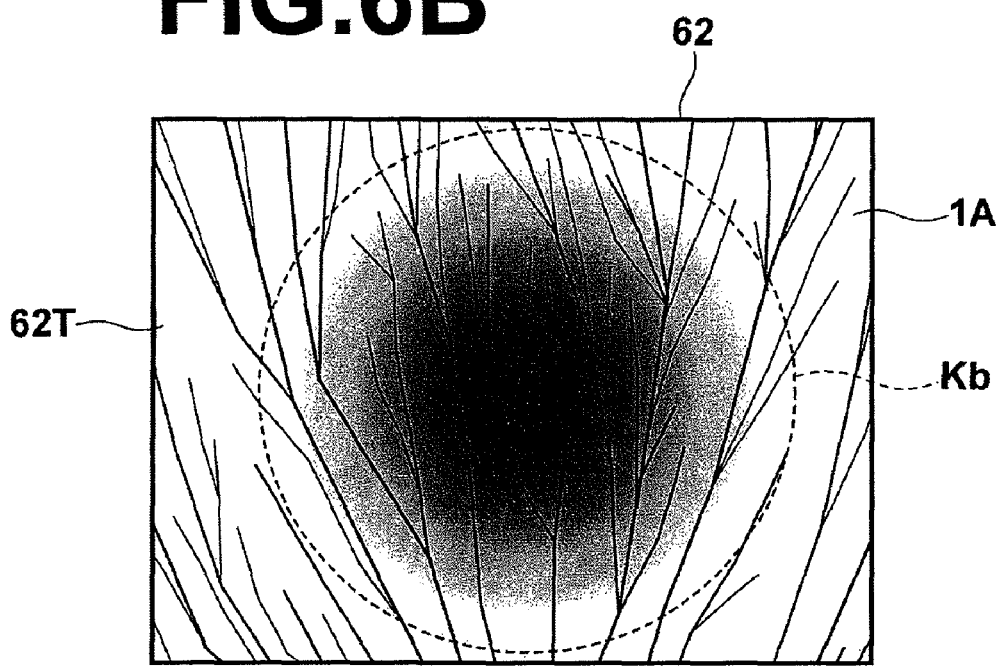
FIG. 6B is a diagram that illustrates a radiation image following automatic adjustment of the imaging magnification rate and the imaging position.

FIG. 6A and FIG. 6B are diagrams that illustrate the manner in which the imaging magnification rate and the imaging position are automatically adjusted according to specification of a region of interest within radiation images obtained by low dosage radiation imaging. FIG. 6A is a diagram that illustrates a radiation image prior to automatic adjustment of the imaging magnification rate and the imaging position. FIG. 6B is a diagram that illustrates a radiation image following automatic adjustment of the imaging magnification rate and the imaging position.

First, an operator specifies a region of interest 1b within a radiation image, which is obtained by low dosage radiation imaging, using the touch panel 62T which is integrated with the radiation image display section 62, as illustrated in FIG. 6A.

Here, it is desirable for the region of interest Kb to be specified within a plurality of radiation images, which are obtained with the imaging section 20 at different rotational positions about the axis of rotation C1. By specifying the region of interest Kb in this manner, the position and size of the region of interest Kb can be specified more accurately.

Next, the region of interest information obtaining section 42 obtains region of interest information that indicates the size and position of the region of interest Kb within the breast 1A, which is specified in the radiation image being displayed by the radiation image display section 62. Here, the region of interest information obtaining section 42 also functions as a region of interest detecting means for detecting the region of interest Kb.

The position calculating section 44 calculates the positions for the radiation source 22 and the detecting panel 24 with respect to the axis of rotation C1 such that the radiation image appropriately includes the region of interest Kb. The position calculating section 44 also calculates the position of the imaging section 20 with respect to the region of interest Kb at which the axis of rotation C1 passes through the region of interest.

Note that in the case that a radiation image, which is obtained by low dosage radiation imaging, appropriately includes the region of interest Kb, a radiation image obtained by normal dosage radiation imaging will also appropriately include the region of interest Kb.

Thereafter, the results of calculations by the position calculating section 44 are input to the imaging magnification rate control section 46 and the imaging position control section 48.

The imaging position control section 48 to which the results of calculations are input controls the XYZ table 28 via the controller, to position the imaging section 20 with respect to the region of interest Kb. That is, the imaging section 20 is positioned such that the axis of rotation C1 passes through the region of interest Kb and the region of interest Kb is positioned at the center of the radiation image. After this positioning operation, the adjustment of the imaging position is complete. That is, the moving section 90 functions to move the axis of rotation C1 to the position of the region of interest Kb which is detected by the region of interest information obtaining section 42 functioning as the region of interest detecting section.

Meanwhile, the imaging magnification rate control section 46 to which the results of calculations are input controls the slide table unit 80 via the controller 68, and positions the radiation source 22 and the detecting panel 24 with respect to the axis of rotation C1. After this positioning operation, the adjustment of the imaging magnification rate is complete. In this manner, the moving section 90 functions to move the radiation source 22 and the detecting panel 24 to the positions calculated by the position calculating section 44.

As a result, the radiation image displayed by the radiation image display section 62 appropriately includes the region of interest Kb, as illustrated in FIG. 6B. Thereby, radiation CT imaging, which is capable of obtaining radiation images that appropriately represent the region of interest Kb, is enabled.

Note that the detecting panel 24 is that which records a two dimensional radiation image that represents the entirety of a subject when it receives a single irradiation of radiation which has passed through the subject. In addition, it is desirable for the imaging section to not be moved in the direction of the axis of rotation during radiation CT imaging. Further, it is desirable for the imaging section to not be moved in the directions perpendicular to the axis of rotation during radiation CT imaging.

Note that the subject of radiation imaging operations is not limited to breasts, and may be the limbs or the thoracic region of a patient.

As described above, the CT apparatus of the present invention can adjust the imaging magnification rate during radiation imaging easily.

Hereinafter, information to complement the contents of this specification will be listed. Note that a portion of the information below will overlap the contents of this specification.

First, the entirety of the subject is viewed by radiation imaging using low dosage radiation, to determine a region of interest. Then, the detecting panel is moved in the aforementioned facing direction to enlarge the radiation image to be obtained, or moved to obtain a radiation image at substantially actual size (by causing the detecting panel to approach the subject).

The imaging magnification rate is adjusted by changing the relative relationships among the radiation source, the breast which is the subject, and the detecting panel.

The mirror is placed between the radiation source and the subject, and an imaging element (such as a CCD) is provided at a position which is a mirror image of the focal point of the radiation source, in order to enable confirmation of the central imaging position. Radiation imaging may be performed with the mirror between the radiation source and the subject, or the mirror may be removed during radiation imaging.

There are various manners in which the image of the subject is displayed. The image of the subject may be displayed on a remote monitor, or a monitor provided in the vicinity of the radiation CT apparatus.

Although this will result in the apparatus becoming larger, the radiation CT apparatus may be configured to change the imaging magnification rate by moving only one of the radiation source and the detecting panel, to change the distance to the axis of rotation therefrom.

It is desirable for a safety mechanism to be provided in the radiation CT apparatus. Examples of safety mechanisms include those in which an optical sensor measures the distance to the subject, detects movement toward the subject, or detects contact with the subject, and operations are ceased based on the measurement or detection.

Sequential imaging may be performed while performing the "see through function" employing low dosage radiation, without moving the imaging system.

It is desirable for the imaging section to be movable in the vertical direction, which is the direction of the axis of rotation.

Relative movement in the directions perpendicular to the direction of the axis of rotation may be performed by moving the bed portion (relative movement in the vertical direction may be performed by moving the imaging system). The patient may be asked to move, but this would result in a burden on the patient.

The detecting surface of the detecting panel may be a planar surface or a curved surface.

The interval between the radiation source and the detecting panel may be fixed. In this case, however, the detecting panel and the radiation source are to be movable away from the axis of rotation.

Movements in the direction of the axis of rotation and the directions perpendicular thereto are fine adjustments, and the main operation is movement in the facing direction. The main objective of the radiation C apparatus of the present invention is to obtain enlarged images of regions of interest.

Note that in the case that adjustments are performed on both the imaging magnification rate and the imaging position, it is desirable for the imaging position to be adjusted first to set the central portion of the subject on the axis of rotation, then to adjust the imaging magnification rate.

Radiation imaging using low dosage radiation may be utilized for preliminary irradiation (a preliminary process for positioning), and for viewing the subject while zoomed out (to display an image of the entirety of a breast, for example).

The preliminary irradiation may be performed with the objective of AEC (Automatic Exposure Control, to set radiation imaging conditions).

It is desirable for radiation CT imaging to be performed such that the emission axis of radiation that passes through the emission point of radiation from the radiation source and is perpendicular to the axis of rotation (and intersects the axis of rotation) is set to pass through the region of interest within the subject. In addition, it is desirable for radiation CT imaging to be performed in a state in which the axis of rotation of the imaging section and the center of the region of interest are substantially matched.

It is desirable for the imaging magnification rate to be displayed.

Further, it is desirable for a viewing scale to be displayed by the radiation image display section 62 of the console 60, according to the imaging magnification rate.

The operator specifies a region of interest Kb that he or she wishes to view on a preliminary radiation image (low dosage radiation image) or on an optical image (visible light image). The moving mechanisms operate to adjust the imaging magnification rate and the imaging position, according to the specified region of interest.

Here, the region of interest Kb may be set automatically by CAD (Computer Aided Detection). That is, a CAD system may analyze a radiation image to detect diseased portions (microcalcification clusters or tumor patterns), and set positions which are possibly disease sites as regions of interest Kb.

The present invention is not limited to radiation CT imaging of breasts. The present invention may also be applied to cone beam radiation CT apparatuses (radiation CT apparatuses having flat panel sensors, onto which X-rays having a conical distribution are irradiated to perform radiation imaging) which are utilized in cases that the subjects of radiation imaging are thoracic regions and limbs. Note that in common radiation CT apparatuses, radiation emitted from radiation sources have linear X-ray distributions, which are received by linear sensors.

Hereinafter, the construction of the radiation source 22 will be described.

FIG. 7 is a diagram that illustrates the interior of the radiation source 22 of a cone beam radiation CT apparatus. As illustrated in FIG. 7, a collimator wing 22b and a collimator wing 22c are moved in a direction perpendicular to the irradiation direction of radiation, to obtain an irradiation angle in which the irradiation field of radiation is focused, based on the size and the position of a region of interest.

Radiation emitted from an X-ray tube 22a is irradiated with a conical distribution. In the case that the aperture of the collimator of the radiation source is to be made greater, the irradiation field can be made wider by increasing the distance between the collimator wing 22b and the collimator wing 22c. In the case that the aperture of the collimator of the radiation source is to be made smaller, the irradiation field can be made narrower by decreasing the distance between the collimator wing 22b and the collimator wing 22c.

It is desirable for the collimator wing 22b and the collimator wing 22c to be moved such that radiation can be irradiated appropriately onto the range of the detected region of interest. By focusing the irradiation field in this manner, the dosage of radiation irradiated on the patient can be minimized.

After radiation imaging is completed and the obtained radiation images are to be stored in the image processing section 72 or a recording medium, image data that represents the region of interest or a portion of the region of interest may be stored at a high resolution, and image data that represents portions of the subject other than the region of interest may be stored at a normal resolution. In this case, the image data can be stored more efficiently within recording media. Recording media include paper, magnetic disks, semiconductor memories, and other various media.

What is claimed is:

1. A radiation CT apparatus, comprising:
a radiation source that emits radiation in a conical manner; and
a detecting panel for detecting the radiation;
the radiation source and the detecting panel being provided facing each other with an axis of rotation that passes though a predetermined position therebetween;
radiation images of a subject placed at the predetermined position being imaged while rotating the radiation source and the detecting panel about the axis of rotation; and
the position of at least one of the radiation source and the detecting panel being movable in the direction that they face each other in; further comprising:
region of interest information obtaining means, for obtaining region of interest information that represents the size and position of a region of interest within the radiation images, employing the radiation images of the subject;
position calculating means, for calculating positions for the radiation source and the detecting panel along the direction that they face each other in that enable appropriate radiation imaging of the region of interest, employing the region of interest information; and
moving means, for moving the radiation source and the detecting panel to the positions calculated by the position calculating means.

2. A radiation CT apparatus as defined in claim 1, wherein:
the region of interest information obtaining means obtains the information regarding the region of interest using images obtained by imaging in at least two directions, from among the radiation images.

3. A radiation CT apparatus as defined in claim 1, further comprising:
a visible light imaging means for performing visible light imaging that converts the propagating region of radiation, which is emitted from the radiation source and detected by the detecting panel, to the visible range; and
a visible light image display means for displaying visible light images obtained by the visible light imaging.

4. A radiation CT apparatus as defined in claim 3, wherein:
the region of interest information obtaining means obtains the information regarding the region of interest using one of the radiation images and the visible images obtained by imaging in at least two directions.

5. A radiation CT apparatus as defined in claim 1, further comprising:
means for controlling the aperture of a collimator of the radiation source such that the irradiation field of radiation irradiation is concentrated, based on the size and the position of the region of interest.

6. A radiation CT apparatus as defined in claim 1, wherein:
the radiation source and the detecting panel are configured to be movable in the direction of the axis of rotation.

7. A radiation CT apparatus as defined in claim 1, further comprising:
imaging magnification rate obtaining means, for obtaining an imaging magnification rate from the ratio of the distance from the axis of rotation to the radiation source and the distance from the axis of rotation to the detecting panel; and imaging magnification rate display means, for displaying the imaging magnification rate.

8. A radiation CT apparatus as defined in claim 1, further comprising:

a radiation source distance measuring means, for measuring the distance from the subject placed at the predetermined position to the radiation source; and radiation source movement prohibiting means, for prohibiting movement of the radiation source toward the axis of rotation when the distance measured by the radiation source distance measuring means becomes less than or equal to a predetermined value.

9. A radiation CT apparatus as defined in claim 1, further comprising:

a detecting panel distance measuring means, for measuring the distance from the subject placed at the predetermined position to the detecting panel; and detecting panel movement prohibiting means, for prohibiting movement of the detecting panel toward the axis of rotation when the distance measured by the detecting panel distance measuring means becomes less than or equal to a predetermined value.

10. A radiation CT apparatus as defined in claim 1, further comprising:

radiation source contact detecting means, for detecting contact between the radiation source and the subject placed at the predetermined position; and at least one of:

radiation source movement prohibiting means, for prohibiting movement of the radiation source toward the subject based on the detection of contact; and radiation source contact notification means, for issuing notification regarding the detection of contact between the radiation source and the subject.

11. A radiation CT apparatus as defined in claim 1, further comprising:

detecting panel contact detecting means, for detecting contact between the detecting panel and the subject placed at the predetermined position; and at least one of:

detecting panel movement prohibiting means, for prohibiting movement of the detecting panel toward the subject based on the detection of contact; and detecting panel contact notification means, for issuing notification regarding the detection of contact between the detecting panel and the subject.

12. A radiation CT apparatus as defined in claim 1, further comprising:

means for storing image data that represents portions of the subject other than the region of interest at a predetermined resolution, and for storing image data that represents the region of interest within the subject at a resolution higher than the predetermined resolution.

13. A radiation CT apparatus, comprising:

a radiation source that emits radiation in a conical manner; and a detecting panel for detecting the radiation;

the radiation source and the detecting panel being provided facing each other with an axis of rotation that passes though a predetermined position therebetween;

radiation images of a subject placed at the predetermined position being imaged while rotating the radiation source and the detecting panel about the axis of rotation; and the position of at least one of the radiation source and the detecting panel being movable in the direction that they face each other in; further comprising:

region of interest detecting means, for detecting the position of a region of interest within the radiation images, employing the radiation images that represent the subject; and means for moving the axis of rotation to the detected region of interest.

14. A radiation CT apparatus as defined in claim 13, further comprising:

position calculating means, for calculating positions for the radiation source and the detecting panel along the direction that they face each other in that enable appropriate radiation imaging of the region of interest, employing the size and the position of the region of interest; and moving means, for moving the radiation source and the detecting panel to the positions calculated by the position calculating means.

15. A radiation CT apparatus as defined in claim 13, wherein:

the region of interest detecting means detects the information regarding the region of interest using images obtained by imaging in at least two directions, from among the radiation images.

16. A radiation CT apparatus as defined in claim 13, further comprising:

a visible light imaging means for performing visible light imaging that converts the propagating region of radiation, which is emitted from the radiation source and detected by the detecting panel, to the visible range; and a visible light image display means for displaying visible light images obtained by the visible light imaging.

17. A radiation CT apparatus as defined in claim 16, wherein:

the region of interest detecting means detects the information regarding the region of interest using one of the radiation images and the visible images obtained by imaging in at least two directions.

18. A radiation CT apparatus as defined in claim 13, further comprising:

means for controlling the aperture of a collimator of the radiation source such that the irradiation field of radiation irradiation is concentrated, based on the size and the position of the region of interest.

19. A radiation CT apparatus as defined in claim 13, wherein:

the radiation source and the detecting panel are configured to be movable in the direction of the axis of rotation.

20. A radiation CT apparatus as defined in claim 13, further comprising:

imaging magnification rate obtaining means, for obtaining an imaging magnification rate from the ratio of the distance from the axis of rotation to the radiation source and the distance from the axis of rotation to the detecting panel; and imaging magnification rate display means, for displaying the imaging magnification rate.

21. A radiation CT apparatus as defined in claim 13, further comprising:

a radiation source distance measuring means, for measuring the distance from the subject placed at the predetermined position to the radiation source; and radiation source movement prohibiting means, for prohibiting movement of the radiation source toward the axis of rotation when the distance measured by the radiation source distance measuring means becomes less than or equal to a predetermined value.

22. A radiation CT apparatus as defined in claim 13, further comprising:
   a detecting panel distance measuring means, for measuring the distance from the subject placed at the predetermined position to the detecting panel; and
   detecting panel movement prohibiting means, for prohibiting movement of the detecting panel toward the axis of rotation when the distance measured by the detecting panel distance measuring means becomes less than or equal to a predetermined value.

23. A radiation CT apparatus as defined in claim 13, further comprising:
   radiation source contact detecting means, for detecting contact between the radiation source and the subject placed at the predetermined position; and at least one of:
   radiation source movement prohibiting means, for prohibiting movement of the radiation source toward the subject based on the detection of contact; and
   radiation source contact notification means, for issuing notification regarding the detection of contact between the radiation source and the subject.

24. A radiation CT apparatus as defined in claim 13, further comprising:
   detecting panel contact detecting means, for detecting contact between the detecting panel and the subject placed at the predetermined position; and at least one of:
   detecting panel movement prohibiting means, for prohibiting movement of the detecting panel toward the subject based on the detection of contact; and
   detecting panel contact notification means, for issuing notification regarding the detection of contact between the detecting panel and the subject.

25. A radiation CT apparatus as defined in claim 13, further comprising:
   means for storing image data that represents portions of the subject other than the region of interest at a predetermined resolution, and for storing image data that represents the region of interest within the subject at a resolution higher than the predetermined resolution.

26. An imaging method that enables imaging magnification rates to be changed, to be employed by a radiation CT apparatus comprising: a radiation source that emits radiation in a conical manner; and a detecting panel for detecting the radiation; the radiation source and the detecting panel being provided facing each other with an axis of rotation that passes though a predetermined position therebetween; and the position of at least one of the radiation source and the detecting panel being movable in the direction that they face each other in; comprising the steps of:
   imaging radiation images of a subject placed at the predetermined position while rotating the radiation source and the detecting panel about the axis of rotation;
   obtaining region of interest information that represents the size and position of a region of interest within the radiation images, employing the radiation images of the subject;
   calculating positions for the radiation source and the detecting panel along the direction that they face each other in that enable appropriate radiation imaging of the region of interest, employing the region of interest information; and
   moving the radiation source and the detecting panel to the positions calculated by the position calculating means.

27. An imaging method that enables imaging magnification rates to be changed, to be employed by a radiation CT apparatus comprising: a radiation source that emits radiation in a conical manner; and a detecting panel for detecting the radiation; the radiation source and the detecting panel being provided facing each other with an axis of rotation that passes though a predetermined position therebetween; and the position of at least one of the radiation source and the detecting panel being movable in the direction that they face each other in; comprising the steps of:
   imaging radiation images of a subject placed at the predetermined position while rotating the radiation source and the detecting panel about the axis of rotation;
   detecting the position of a region of interest within the radiation images, employing the radiation images that represent the subject; and
   moving the axis of rotation to the detected region of interest.

* * * * *